(12) United States Patent
Gassman et al.

(10) Patent No.: US 9,072,824 B2
(45) Date of Patent: Jul. 7, 2015

(54) AUTOMATED METHODS OF WHOLE BLOOD PROCESSING

(75) Inventors: Christopher D. Gassman, Crystal Lake, IL (US); Andres Pasko, Genoa City, WI (US); Walter T. Watts, Arlington Heights, IL (US)

(73) Assignee: Fenwal, Inc., Lake Zurich, IL (US)

( * ) Notice: Subject to any disclaimer, the term of this patent is extended or adjusted under 35 U.S.C. 154(b) by 611 days.

(21) Appl. No.: 13/446,046

(22) Filed: Apr. 13, 2012

(65) Prior Publication Data

US 2012/0291867 A1 Nov. 22, 2012

Related U.S. Application Data

(60) Provisional application No. 61/486,867, filed on May 17, 2011.

(51) Int. Cl.
*A61M 1/00* (2006.01)
*F17D 3/00* (2006.01)
(Continued)

(52) U.S. Cl.
CPC .............. *A61M 1/02* (2013.01); *Y10T 137/8593* (2015.04); *Y10T 137/0318* (2015.04); *A61M 1/0209* (2013.01); *A61M 1/0272* (2013.01);
(Continued)

(58) Field of Classification Search
CPC .................. A61M 2205/3331; A61M 2205/15; A61M 5/1483; A61M 1/0209; A61M 1/02; A61M 1/029; A61M 5/1486; A61M 1/0218; A61M 2209/084; A61M 1/0272; A61M 1/0281; A61M 2205/331; A61M 39/143; A61M 5/1417; Y10T 137/8593; Y10T 137/0318

USPC .......... 210/85, 86, 97, 10, 103, 134, 143, 252, 210/256, 257.1, 258; 222/95, 105, 152, 52, 222/53; 137/1, 561 R
See application file for complete search history.

(56) References Cited

U.S. PATENT DOCUMENTS 5,547,108 A 8/1996 Gsell
5,695,653 A 12/1997 Gsell
(Continued)

FOREIGN PATENT DOCUMENTS

GB 2 298 933 A 9/1996
WO WO2004/032999 A1 4/2004

OTHER PUBLICATIONS

Extended European Search Report for European Patent Application No. 12164621.0, dated Aug. 30, 2013.

*Primary Examiner* — John Kim
(74) *Attorney, Agent, or Firm* — Cook Alex, Ltd.

(57) ABSTRACT

A system is provided for controlling fluid flow in a flow circuit of the type including at least two flexible containers which are fluidly connected by a conduit. The system includes a pressure chamber having an interior which receives one of the containers of the flow circuit. The pressure chamber has at least one port which communicates between the interior of the pressure chamber and the outside environment and receives at least a portion of the conduit of the flow circuit. The pressure chamber also includes a pressure/vacuum source for increasing the pressure in the interior of the pressure chamber above atmospheric pressure and decreasing the pressure in the interior of the pressure chamber below atmospheric pressure. The pressure chamber may include other elements, such as interface detectors, clamping devices, sealing devices, and access devices for automatically processing fluid, such as separated blood.

15 Claims, 6 Drawing Sheets

(51) Int. Cl.
*A61M 1/02* (2006.01)
*A61M 5/148* (2006.01)
*A61M 5/14* (2006.01)
*A61M 39/14* (2006.01)

(52) U.S. Cl.
CPC ............ *A61M 1/0281* (2013.01); *A61M 1/029* (2013.01); *A61M 5/1486* (2013.01); *A61M 2205/15* (2013.01); *A61M 2205/331* (2013.01); *A61M 2205/3331* (2013.01); *A61M 2209/084* (2013.01); *A61M 5/1417* (2013.01); *A61M 39/143* (2013.01); *A61M 1/0218* (2014.02)

(56) References Cited

U.S. PATENT DOCUMENTS

| 6,994,790 | B2 | 2/2006 | Corbin, III et al. |
| 2003/0195104 | A1 | 10/2003 | Hlavinka |
| 2005/0113237 | A1 | 5/2005 | Rosiello et al. |
| 2007/0135765 | A1 | 6/2007 | Miller |

FIG. 10

AUTOMATED METHODS OF WHOLE BLOOD PROCESSING

CROSS-REFERENCE TO RELATED APPLICATION

This application claims priority from and the benefit of U.S. provisional patent application Ser. No. 61/486,867, filed May 17, 2011, which is hereby incorporated herein by reference.

BACKGROUND

1. Field of the Disclosure

The present subject matter relates to systems and methods for automated expression of fluid from a container. More particularly, the present subject matter relates to systems and methods for automated expression of a fluid from and/or into a blood component-containing container.

2. Description of Related Art

Whole blood is typically collected from donors in what is commonly called a manual collection procedure. In such a procedure, whole blood is collected directly from the donor into a primary collection container. The whole blood may be separated into its constituents by various means, including centrifugation. Once the blood has been separated into its component parts, the component may be variously disposed of, depending on the nature of the particular processing procedure. For example, one or more of the separated components (e.g., red cells) may be stored for later administration to a patient and other components (e.g., plasma or platelets) may be collected and pooled with like components from other donors for administration or processing at a later time. In other procedures, one of the separated components may be processed and returned to the blood source, as is the case in automated therapeutic plasma exchanges or platelet-only collections.

In manual collection, blood is typically drawn from a blood source (such as a healthy donor) into a pre-assembled and pre-sterilized fluid circuit having a number of flexible containers connected together by tubing. The whole blood is typically directed into a primary collection container, where it is mixed with an amount of anticoagulant. After initial collection, the primary container, with any attached satellite containers, is transported to a processing facility which may be at the same site as the collection, or elsewhere, for further processing. There, the anticoagulated blood is separated into its components (e.g., by centrifugation) and one or more of the components is flowed or expressed out of the primary container. In certain blood processing systems employed in such processing, an integrated apparatus is provided for both separating the blood into its constituents and then expressing one or more of the constituents from the container. One possible disadvantage with existing blood processing systems is that they typically rely on moving mechanical parts (e.g., peristaltic pumps), which are subject to simple mechanical failure due to age or any of a number of other reasons. If even one of the many parts of the system malfunctions, the entire system may become unusable, thereby defeating one of the purposes of an "all-in-one" or integrated processing system.

An alternative to "all-in-one" type blood processing systems is the use of separate separation and expression devices, such as a centrifuge (for blood separation) and an expresser (for expression of a blood component from a container having a plurality of blood components). An exemplary system for separately fractionating blood and expressing blood components is described in U.S. Pat. No. 6,994,790 to Corbin, Ill. et al., which is incorporated herein by reference. Typically, the expresser includes a pair of parallel or hingedly connected plates. If the plates are parallel, the container is placed therebetween and the plates are moved toward each other to exert pressure on the container and express one or more of the blood components out of a port or opening of the container. If the plates are hingedly connected, the container is placed in the space between the plates and then the plates are pivoted toward each other to exert pressure on the container and thereby express one or more of the blood components out of a port or opening of the container. Other known expression devices include, but are not limited to, those of the type described in U.S. Pat. Nos. 5,547,108 and 5,695,653 to Gsell et al., both of which are incorporated herein by reference.

Another disadvantage of known processing systems and expressers is that it will sometimes be desirable to do more than merely express a blood component from a container holding a plurality of blood components. For example, it may be advantageous to express a component into a satellite container, add a storage solution or additive to a blood component remaining in the original container, mix the component and additive, and then express any excess air from the containers. Known expressers and systems are not suited for automating all of these procedures and typically require substantial operator intervention and oversight to carry out all of the desired processing steps. Manual intervention potentially includes the risk of human error. It would be advantageous to avoid or limit such a risk by providing a single device capable of automating all of the necessary post-collection and/or post-separation processing steps.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a system is provided for controlling fluid flow in a flow circuit of the type including at least two flexible containers and at least one conduit, with each container being fluidly connected to at least one other container by a conduit. The system includes a pressure chamber having an interior which receives at least one of the containers of the flow circuit and at least one port which communicates between the interior of the pressure chamber and the outside environment. The port is adapted to receive at least a portion of one of the conduits of the flow circuit. The pressure chamber further includes a pressure/vacuum source for providing a pressure in the interior of the pressure chamber ranging between above atmospheric pressure and below atmospheric pressure and for changing the pressure in the interior of the pressure chamber.

In another aspect, a system is provided for controlling fluid flow in a flow circuit of the type including at least two flexible containers and at least one conduit, with each container being fluidly connected to at least one other container by a conduit. The system includes a pressure chamber having an interior which receives at least one of the containers of the flow circuit and at least one port which communicates between the interior of the pressure chamber and the outside environment. The port is adapted to receive at least a portion of one of the conduits of the flow circuit. The port includes an associated interface detector, automated clamping device, automated sealing device, and automated access device. The pressure chamber further includes a pressure/vacuum source for providing a pressure in the interior of the pressure chamber ranging between above atmospheric pressure and below atmospheric pressure and for changing the pressure in the interior of the pressure chamber. A controller of the system is programmed to control the interface detector, the automated clamping device, the automated sealing device, the automated access device, and the pressure/vacuum source.

In yet another aspect, a method is provided for controlling fluid flow in a flow circuit. The method includes providing a flow circuit having a plurality of flexible containers fluidly connected by a plurality of conduits. At least one of the containers includes a fluid. At least one of the containers is inserted into a pressure chamber programmable to have an interior pressure in a range between greater than atmospheric pressure and less than atmospheric pressure. At least one of the other containers is positioned outside of the pressure chamber and a vacuum or positive pressure is applied to the container in the pressure chamber, thereby expressing fluid from one of the fluid-containing containers to at least one of the other containers through one of the conduits.

DESCRIPTION OF THE ILLUSTRATED EMBODIMENTS

The embodiments disclosed herein are exemplary only, and the subject matter described herein may be embodied in various forms. Therefore, specific details disclosed herein are not to be interpreted as limiting the subject matter as defined in the accompanying claims.

FIGS. 1-4 show a fluid expression system 10 which includes a flow circuit 12 and a pressure chamber 14 according to aspects of the present disclosure. The pressure chamber 14 is preferably provided as a durable unit or part of a durable system, while the flow circuit 12 is typically provided as a single-use, disposable item which may be used in combination with a fluid separation device (not illustrated) and the pressure chamber 14, as will be described in greater detail below. As used herein, the term "fluid" is to be construed broadly to include not only liquid, but also gas and mixtures of liquid and gas.

A. Flow Circuit

The flow circuit 12 may be provided according to known design or it may be a novel configuration (e.g., being specially suited to be used in combination with the pressure chamber 14). The illustrated flow circuit 12 comprises a plurality of flexible container 16, 18, 20, and 22 which are fluidly connected by tubing or fluid conduits 24a-24c. The flow circuit 12 of FIGS. 1-4 and the flow circuit 12a of FIG. 5 are illustrated with four containers, but it is also within the scope of the present disclosure to provide a flow circuit having more than four containers (FIG. 9) or less than four containers (FIG. 10). The functionality of the different flow circuits will be described in greater detail below.

It may be advantageous for one of the containers, illustrated in FIGS. 1-4 as container 16, to be fluidly connected to all of the other containers 18, 20, and 22 by the conduits 24a-24c. The flow circuit 12 may be preassembled and pre-sterilized or user-assembled using appropriate sterile connection devices and/or components. As shown in FIGS. 1-4, one or more of the conduits 24a-24c may include an associated closure element 26a-26c that is operable to isolate, usually initially, the various containers 16, 18, 20, and 22 from each other. When a closure element 26a-26c is actuated, it opens (if pre-closed) the associated conduit 24a-24c for fluid flow therethrough, thereby fluidly connecting the containers 16, 18, 20, and/or 22 which are connected to the opposite ends of the conduit 24a-24c. The closure elements 26a-26c may be of various configurations, but in one embodiment, are provided as frangible closure elements (e.g., cannulae) which may be broken and opened manually or by an automated device to open the associated conduit 24a-24c for fluid communication.

The flow circuit 12 may include additional components in various numbers, arrangements, and orientations without departing from the scope of the present disclosure. For example, the flow circuit 12 of FIGS. 1-4 is provided with a filtration device 28 (e.g., a white cell reduction filter) inline with one of the conduits 24c. While the filtration device 28 is illustrated as being inline with conduit 24c, it is also within the scope of the present disclosure for the filtration device 28 (or an additional filtration device) to be incorporated into any of the other conduits. In an alternative flow circuit 12a (FIG. 5), an additional conduit 24d is provided, with the conduit 24d being connected at its ends to conduit 24c and container 22. Each of conduits 24c and 24d is provided with a valve 30, the use of which will be described in greater detail below. Other components may include, for example, additional filtration subassemblies, directional flow restrictors, cannulae, sample systems, and other disposable components which are known by those of ordinary skill in the art.

B. Pressure Chamber

The pressure chamber 14 may be provided as a stationary device (FIG. 7) configured to be installed and remain in a single location or as a mobile device (FIG. 8) configured to be moved to different locations. It may be variously configured but, in one embodiment, is configured to have the same or similar geometry as the device used to initially separate blood into its constituent parts (e.g., the container or cup or holder of a centrifuge). Such a configuration may facilitate the easy transfer of the separated blood container from the separator to the pressure chamber 14, as will be described in greater detail herein. Other configurations may also be employed, depending on the configuration of the associated flow circuit 12. For example, in one embodiment, the flow circuit 12 may be packaged in a molded or fitted sheath, with the pressure chamber 14 and the container or cup or holder of the centrifuge being shaped and configured to accommodate the sheath and to allow for easy loading and unloading.

The pressure chamber 14 includes an open interior 32 which is configured to receive at least one of the containers of the flow circuit 12. The conduits associated with the container are received by ports 34a, 34b, and 34c which communicate between the interior 32 of the pressure chamber 14 and the outside environment, where at least one of the other containers of the flow circuit 12 is positioned. The pressure chambers 14 of FIGS. 1-6 are illustrated with three ports, but it is also within the scope of the present disclosure to provide a pressure chamber having more than three ports (FIG. 9) or less than three ports (FIG. 10). The use of such differently configured pressure chambers will be described in greater detail herein.

Figure 7:
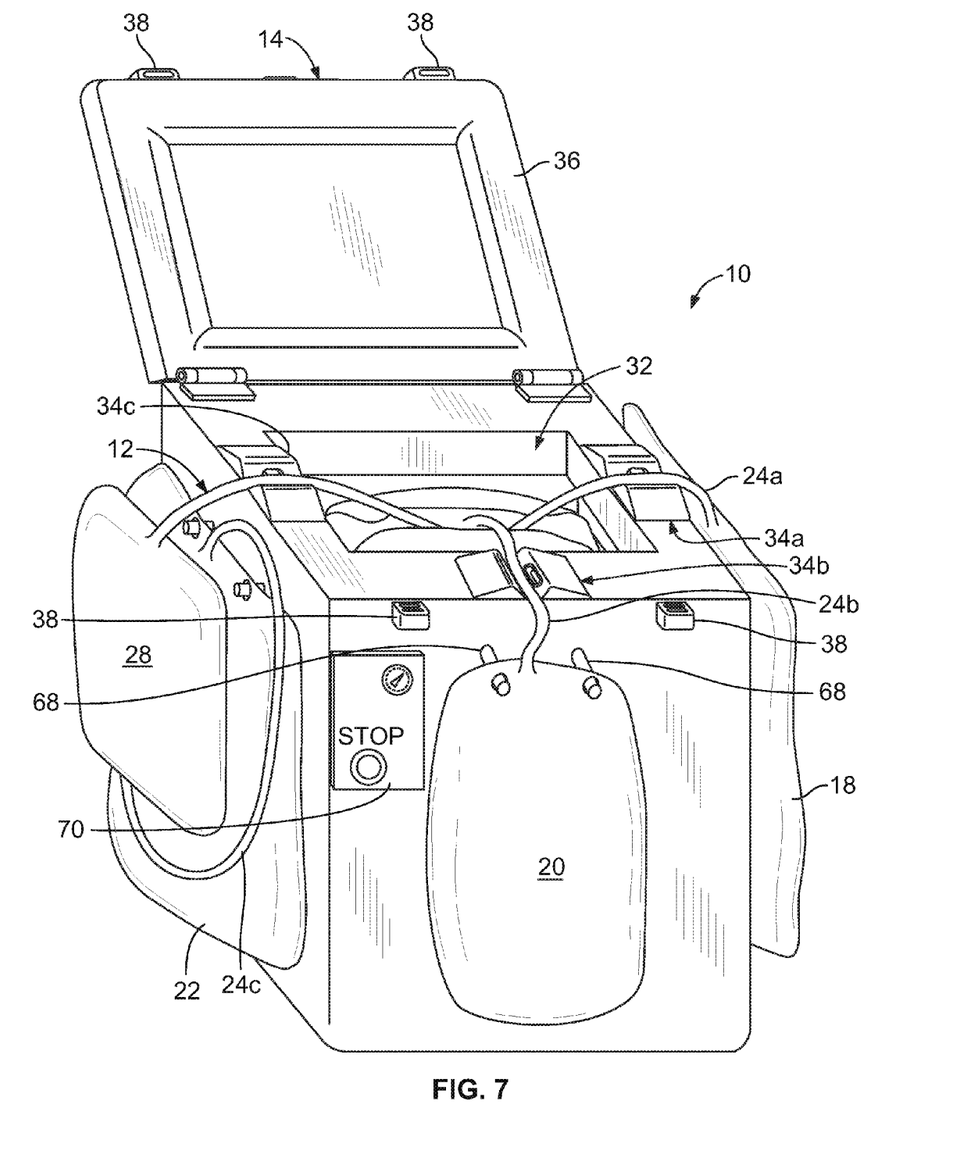
FIG. 7 is a front perspective view of the pressure chamber of FIG. 1, incorporated in a stationary installation.
Figure 8:
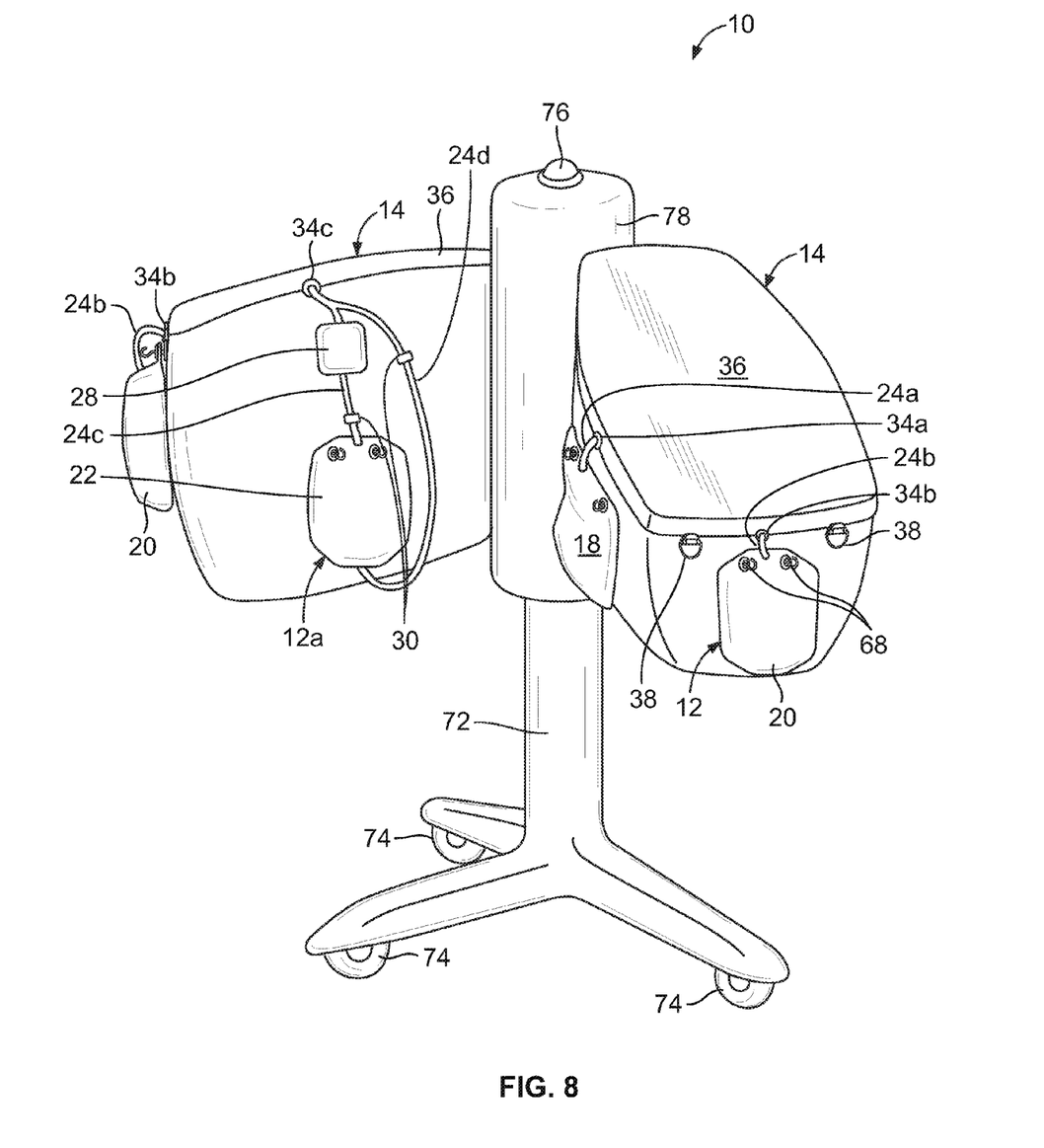
FIG. 8 is a front perspective view of the pressure chamber of FIG. 1, incorporated in a mobile unit.

The pressure chamber 14 may include a chamber base or body and a closure element or lid 36 (FIGS. 7 and 8) which is opened to allow a container to be placed in the interior 32 and then closed to isolate the container from the outside environment. As will be described in greater detail below, an elevated pressure or vacuum is applied within the pressure chamber 14, so the lid 36 may be configured to form an air-tight seal when closed. To promote an air-tight seal, the lid 36 may include a gasket or the like along its perimeter. The lid 36 may also include a lock or latch mechanism 38 for securing the lid 36 in a closed position during operation. As shown in FIGS. 7 and 8, it may be advantageous for the ports 34a, 34b, and 34c to be positioned adjacent to the lid 36. By such a configuration, the conduits of the flow circuit 12 may be loaded into the associated port (FIG. 7) and then the lid 36 may be closed to provide an air-tight seal around the conduits at the ports 34a, 34b, and 34c (FIG. 8). However, the ports 34a, 34b, and 34c may be positioned elsewhere without departing from the scope of the present disclosure.

Each port 34a, 34b, 34c may include a number of associated elements for enhanced functionality and automation. The elements at each port may be integrated together as a single subassembly or may be provided in a plurality of subassemblies each including one or more of the elements or may be individually and separately provided.

In one embodiment, each port includes an associated interface detector 40, an automated clamping device 42, an automated sealing device 44, and an automated access device 46 (FIGS. 1-4). The various devices associated with the ports may be controlled by a controller, provided as a computer or microprocessor or the like. Preferably, the various devices associated with each port operate independently of the devices associated with the other ports, but it is also within the scope of the present disclosure for the controller to be programmed to actuate the various devices simultaneously.

The interface detector 40 may be provided as an optical sensor which detects the transition from one fluid to another (such as from plasma to red cells) by observing a change in one or more of the characteristics of light passing through the conduit associated with the respective port. For example, the interface detector 40 may be configured to sense a change in the reflection, adsorption of a desired electromagnetic frequency, and/or amount of transmission of light through the conduit. When the interface detector 40 detects a transition between two fluids (as broadly defined above), it may send a signal to the controller, which the controller may then use to direct the operation of one or more other elements of the pressure chamber 14, as will be described in greater detail herein.

The automated clamping device 42 may be provided as an element (e.g., a plunger or a roller) which may be brought into and out of contact with the associated conduit to allow or prevent or regulate fluid flow through the conduit. As noted above, the conduits may be provided with closure elements that initially prevent fluid flow through the associated conduit. If the closure element is provided as a one-use item (e.g., a frangible cannula), fluid communication through the associated conduit will be permanently established once the closure element has been actuated, broken, or otherwise opened. By employing the automated clamping device 42 in association with the respective conduit (under control of the controller), fluid communication may be either allowed or prevented through the conduit after the closure element has been actuated. The function(s) of the automated clamping devices 42 during a fluid treatment procedure will be described in greater detail herein.

The automated sealing device 44 may be provided as a control element which may be brought into cooperative contact with the associated conduit and then actuated to close or seal or otherwise permanently prevent fluid flow through the conduit. The manner in which the automated sealing device 44 is actuated to seal the conduit may vary according to the nature of the associated conduit. In one embodiment, the conduits are provided as flexible plastic tubing which may be sealed by compressing the tubing with the automated sealing device 44 and then increasing the temperature of the sealing device 44 or applying RF energy so as to melt the tubing to itself, thereby sealing it and preventing fluid flow therethrough. The function of the automated sealing devices 44 during a fluid treatment procedure will be described in greater detail herein.

The automated access device 46 may be provided as an element or device which actuates the closure element of the associated conduit. The manner in which the automated access device 46 is operated to actuate a closure element may vary according to the nature of the closure element. In one embodiment, the closure elements are provided as frangible cannulae, so the access device 46 is provided as a "cannula breaker or cracker" element which comes into contact with and breaks the cannula (e.g., by bending it beyond its breaking point). The function of the automated access devices 46 during a fluid treatment procedure will be described in greater detail herein.

Figure 6:
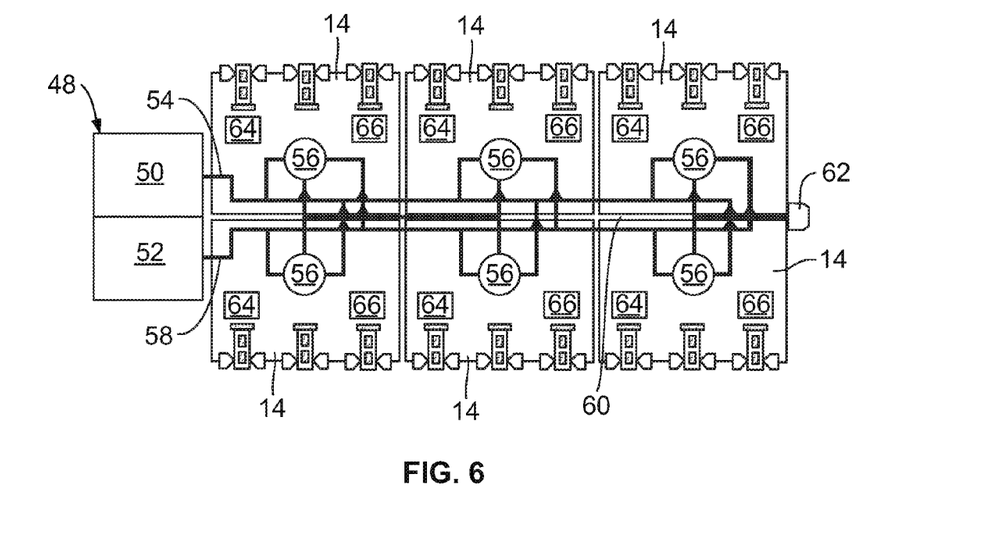
FIG. 6 is a diagrammatic view of a plurality of pressure chambers according to FIG. 1, arranged in a superstructure with the pressure chambers sharing a common pressure/vacuum source.

The pressure chamber 14 further includes a pressure/vacuum source 48 (FIG. 6). The pressure/vacuum source 48 is configured to selectively increase the pressure in the interior 32 of the pressure chamber 14 above atmospheric pressure and decrease the pressure in the interior 32 of the pressure chamber 14 below atmospheric pressure. The pressure/vacuum source 48 may be various configured, provided that it is capable of increasing the pressure in the interior 32 of the pressure chamber 14 above atmospheric pressure and decreasing the pressure in the interior 32 of the pressure chamber 14 below atmospheric pressure. In the illustrated embodiment, the pressure/vacuum source 48 is provided with a pressure compressor or pump 50 suitable for increasing the pressure in the pressure chamber 14 (by increasing the amount of air in the pressure chamber 14) and a pump or vacuum compressor 52 suitable for decreasing the pressure in the pressure chamber 14 (by decreasing the amount of air in the pressure chamber 14).

The pressure/vacuum source 48 may further include a pneumatic circuit capable of alternately controlling a specific pressure and vacuum level. In one embodiment, the pneumatic circuit includes a pressure line or channel 54 associated with the pressure compressor 50 and a valve 56 associated with the pressure line 54. The valve 56 may be a three-way valve capable of being selectively connected to the pressure line 54, a vacuum line 58 associated with the vacuum compressor 52, or a vent line 60 associated with a vent port 62. When it is desirable to increase the pressure in the pressure chamber 14 to a level above atmospheric pressure, the valve 56 may be connected to the pressure line 54 to apply a positive pressure to the interior 32 of the pressure chamber 14. Similarly, when it is desirable to decrease the pressure to a level below atmospheric pressure, the valve 56 may be operated to communicate with the vacuum line 58. When it is desirable to return the pressure chamber 14 to atmospheric pressure, the valve 56 may be operated to communicate with the vent line 60, which vents pressure or vacuum to the outside environment via the associated vent port 62.

The pressure chamber 14 may further include a pressure sensor 64 and/or a leak detector 66 (FIG. 6). As will be described in greater detail herein, the pressure sensor 64 measures the pressure in the pressure chamber 14 and provides such information to the controller. The pressure sensor 64 may also interact with a safety protocol of the controller, which monitors the sensor output and shuts down operation of the pressure chamber 14 if an unsafe pressure or vacuum is detected. The leak detector 66 is capable of detecting the leakage of blood or other fluids from a container in the pressure chamber 14 (e.g., by humidity change). If a leak is detected, the leak detector 66 may send a signal to the controller to shut down operation of the pressure chamber 14. Other elements of the pressure chamber 14 may include exterior hangers 68 for holding the containers not positioned within the interior 32 of the chamber 14 (FIGS. 7 and 8), a user interface or control panel 70 (FIG. 7), a mounting stand 72 with wheels or rollers 74 (FIG. 8), and/or an indicator or beacon 76 for visually and/or audibly expressing the operational status of the pressure chamber 14 or an alarm condition (FIG. 8). The pressure chamber 14 may further include other elements not illustrated or described herein without departing from the scope of the present disclosure.

FIGS. 6 and 8 illustrate a plurality of pressure chambers 14 incorporated into a single system installation or manifold superstructure. In the embodiments of FIGS. 6 and 8, the plurality of pressure chambers 14 are associated with a single pressure/vacuum source 48 (positioned within an enclosure 78 of the mounting stand 72 of FIG. 8). Such manifold systems or superstructures may be useful when processing blood from a number of different sources, as they allow for several containers of separated blood components to be further processed simultaneously. The manifold system or superstructure of FIG. 6 incorporates six pressure chambers 14, which may be useful in combination with known centrifuges designed to simultaneously spin six whole blood collection containers. It should be noted that simultaneous processing does not necessarily imply that the operation of the various individual pressure chambers 14 is synchronized. For example, it may be preferred for the individual pressure chambers 14 to be capable of simultaneous, unsynchronized processing, thereby allowing for more operational versatility.

The various pressure chambers 14 may include individual controllers for controlling the elements of the associated pressure chamber 14 and/or there may be provided a centralized controller for monitoring and controlling the overall operation of the manifold system or superstructure. The controller(s) allow for elements of the various pressure chambers 14 to function independently, thereby allowing for differences in the processing carried out in each pressure chamber 14 (e.g., operating the valves 56 of the pressure chambers 14 at different times), which may be advantageous for a number of reasons. For example, blood physiology characteristics (such as viscosity and hematocrit) vary from whole blood unit to whole blood unit. This variability translates into variable flow/filtration rates per unit. Further, the different pressure chambers 14 may be used to process different amounts of collected blood at the same time. Chamber operational independence also results in improved workflow flexibility, as units of blood may be processed immediately as they are ready rather than in batches of a fixed quantity. Additionally, if one of the chambers malfunctions, it should not affect the functionality of the other chambers.

C. Exemplary Method of Use

FIGS. 1-4 illustrate a method of using a flow circuit 12 and pressure chamber 14. The method illustrated in FIGS. 1-4 is merely exemplary and it is contemplated that the systems may be employed for other processing applications, only some of which will be described herein.

1. Blood Collection And Separation

Prior to introducing or associating the flow circuit 12 with the pressure chamber 14, an amount of blood is drawn into the flow circuit 12 from a blood source such as a donor, patient, or temporary storage container. The blood is located in one or more of the containers of the flow circuit 12, and has preferably already been mixed with an amount of anticoagulant to reduce clotting. In the illustrated embodiment, the anticoagulated whole blood is collected into a single container 16, which is referred to herein as the whole blood collection container. Two of the other containers 18 and 22 (referred to herein as the plasma product container and the red cell product container, respectively) may be empty, while the third other container 20 (referred to herein as the additive solution container) may include an amount of additive solution 80.

The blood in the container 16 is treated to separate it into two or more of its component parts by any of a variety of means, but typically by centrifugation. In the embodiment of FIGS. 1-5, the blood may be separated via "soft spin" or moderate-speed centrifugation into generally two layers—a plasma layer 82 which also contains platelets and white cells and an RBC layer 84 containing concentrated red blood cells. In other embodiments, where the blood is subjected to a hard spin or higher-speed centrifugation, the blood may be separated into three different layers with a buffy coat layer of platelets and white cells located between the plasma and red cells (FIGS. 9 and 10), as will be described in greater detail herein.

2. Installation and Programming

Figure 1:
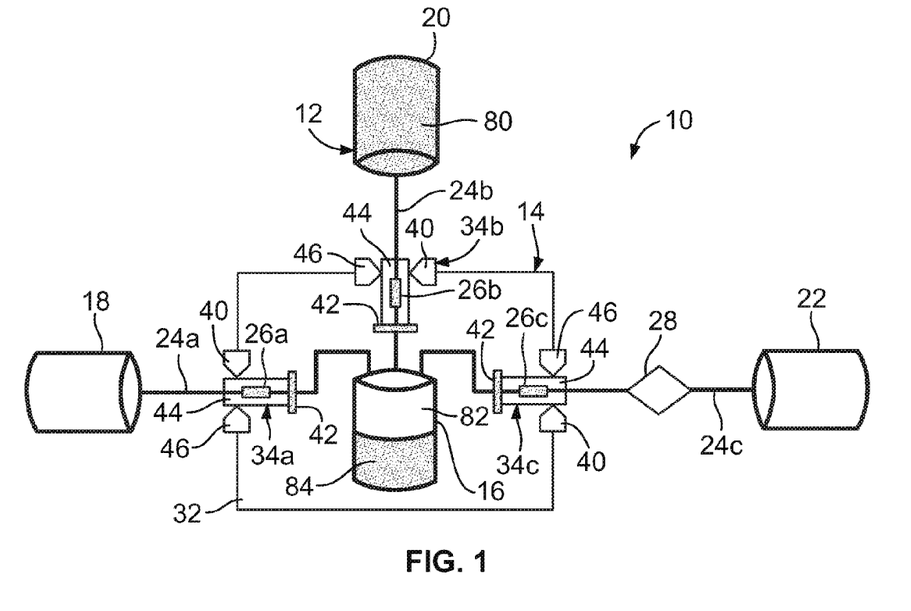
FIG. 1 is a diagrammatic view of an exemplary pressure chamber and flow circuit according to an aspect of the present disclosure.

The whole blood collection container 16 is then placed within the interior 32 of the pressure chamber 14, with the other containers 18, 20, and 22 being positioned outside of the pressure chamber 14 and each conduit passing through an associated port of the pressure chamber 14 (FIG. 1). With the containers and conduits properly positioned, the cover or lid 36 of the pressure chamber 14 is closed or actuated to seal the whole blood collection container 16 within the interior 32 of the pressure chamber 14, isolated from the outside environment. If provided, the operator may use the control panel 70 (FIG. 7) to program the controller and/or verify that the whole blood collection container 16 has been installed and the pressure chamber 14 is ready for further automated processing.

In an alternative embodiment, the controller may be programmed from a remote location, rather than being programmed using the control panel 70. For example, the controller may be configured with Internet or networking capabilities, barcode scanning capabilities, radio-frequency identification ("RFID") reading capabilities, and/or other data management capabilities. In one particular embodiment, a component of the system 10 may be capable of reading an RFID tag or device incorporated into the flow circuit 12 such that, when the RFID device has been read, the system will automatically select the correct expression or processing algorithm.

3. Plasma Expression

Figure 2:
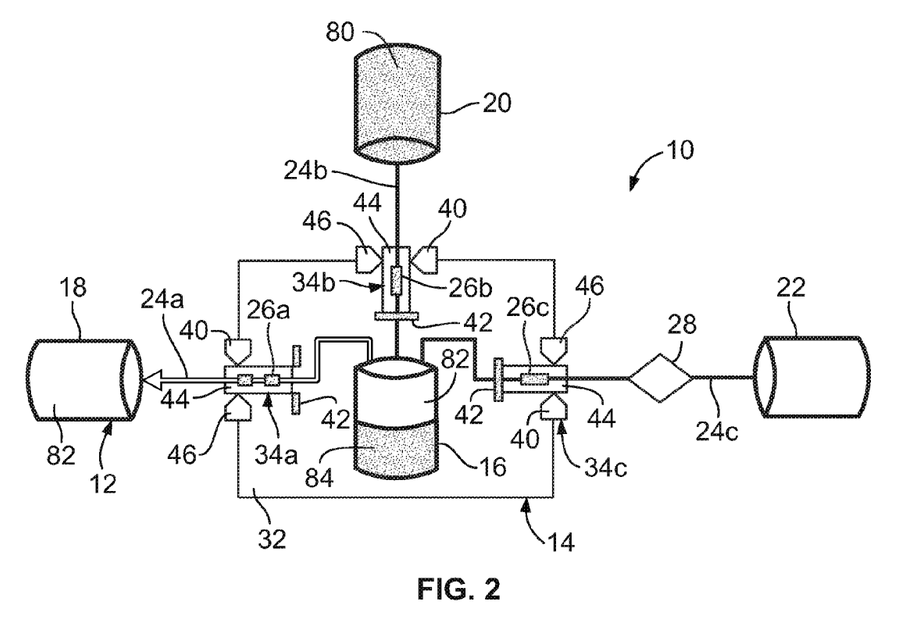
FIG. 2 illustrates the application of pressure to a container in the pressure chamber of FIG. 1 to express fluid out of the container.

The controller of the pressure chamber 14 may be programmed to accommodate different procedures to allow user selection of the desired procedure. As illustrated, the controller begins by actuating all of the automated clamping devices 42 to close (FIG. 1). The controller then actuates the automated access device 46 associated with the conduit 24a from the plasma product container 18 to operate or break the associated closure device 26a (FIG. 2). Operating the closure device 26a allows for fluid communication between the whole blood collection container 16 and the plasma product container 18, although the clamping device 42 temporarily prevents any fluid flow.

The controller then commands the variable pressure/vacuum source 48 to increase the pressure in the interior 32 of the pressure chamber 14 to a desired level above atmospheric pressure. The pressure sensor 64, if provided, monitors the pressure in the pressure chamber 14 and sends a signal to the controller when the pressure reaches the desired level.

With the pressure inside the pressure chamber 14 at the desired level, the controller commands the clamping device 42 to disengage from or release the associated conduit 24a, thereby opening fluid communication between the whole blood collection container 16 and the plasma product container 18. On account of the pressure difference between the two containers 16 and 18, fluid is pushed out of the whole blood collection container 16 and into the plasma product container 18 via the conduit 24a (FIG. 2). With the conduit 24a associated with the top of the whole blood collection container 16 and the plasma layer 82 positioned above the RBC layer 84 in the whole blood collection container 16, the plasma layer 82 is expressed from the collection container 16 and into the plasma product container 18.

Plasma continues flowing to the plasma product container 18 until the interface detector 40 associated with the conduit 24a senses a change in the nature of the light passing through the conduit 24a, such as by observing a significant decrease in the amount of light transmitted through the conduit 24a. This significant decrease in light transmission is indicative of a transition from plasma to cellular components flowing through the conduit 24a. When the interface detector 40 detects the transition, it sends a signal to the controller, which actuates the clamping device 42 to close fluid flow through the conduit 24a. If provided, the controller may actuate the automated sealing device 44 associated with the port 34a to irreversibly seal and optionally sever the conduit 24a between the containers 16 and 18.

4. Addition of Additive Solution

Figure 3:
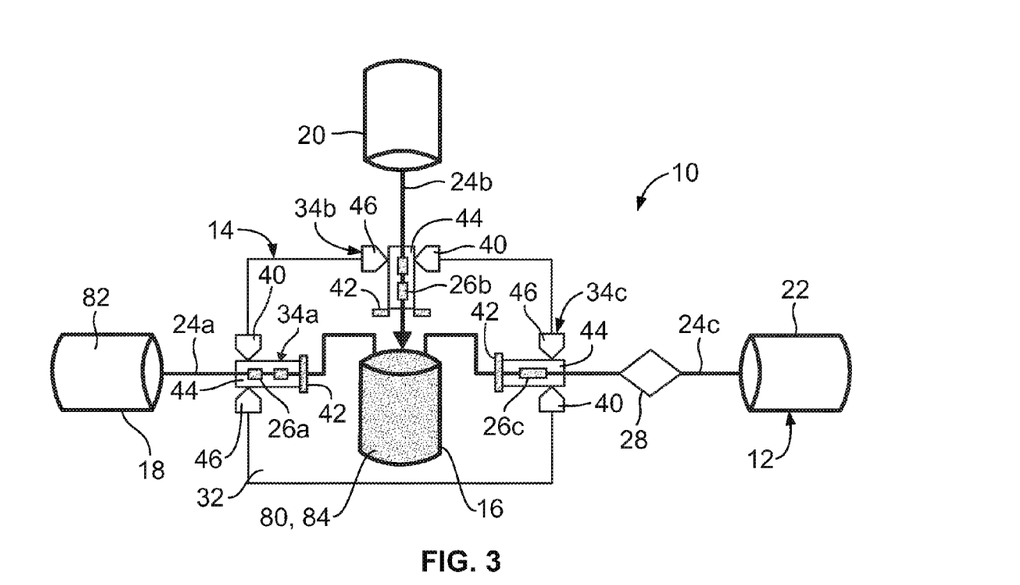
FIG. 3 illustrates the application of a vacuum to a container in the pressure chamber of FIG. 1 to draw fluid into the container.

Next, the controller may actuate the automated access device 46 associated with the conduit 24b from the additive solution container 20 to operate, open, or break the associated closure device 26b (FIG. 3). Operating the closure device 26b allows for fluid communication between the whole blood collection container 16 and the additive solution container 20, although the clamping device 42 temporarily prevents any fluid flow.

The controller then commands the pressure/vacuum source 48 to decrease the pressure in the interior 32 of the pressure chamber 14 to a desired level below atmospheric pressure. The pressure sensor 64 monitors the pressure in the pressure chamber 14 and sends a signal to the controller when the pressure reaches the desired level.

With the pressure inside the pressure chamber 14 at the desired level, the controller commands the clamping device 42 to disengage from the associated conduit 24b, thereby opening fluid communication between the whole blood collection container 16 and the additive solution container 20. On account of the pressure difference between the two containers 16 and 20, the additive solution 80 is drawn or suctioned out of the additive solution container 20 and into the whole blood collection container 16 via the conduit 24b (FIG. 3), where it mixes with the concentrated RBC layer 84. FIG. 3 illustrates the contents of the additive solution container 20 being completely emptied into the whole blood collection container 16, but it is within the scope of the present disclosure for only a portion of the additive solution 80 to be transferred to the whole blood collection container 16.

If the entirety of the additive solution container 20 is to be emptied into the whole blood collection container 16, the operational state of FIG. 3 is maintained until the interface detector 40 associated with the conduit 24b senses a change in the nature of the light passing through the conduit 24a, such as by observing a significant increase in the amount of light transmitted through the conduit 24b. This significant increase in light transmission is indicative of a transition from additive solution 80 to air (or the absence of additive solution 80) flowing through the conduit 24b. When the interface detector 40 detects the transition, it sends a signal to the controller, which actuates the clamping device 42 to close fluid flow through the conduit 24b. If provided, the controller may actuate the automated sealing device 44 associated with the port 34b to irreversibly seal and optionally sever the conduit 24b between the containers 16 and 20.

5. Red Blood Cell Expression

Figure 4:
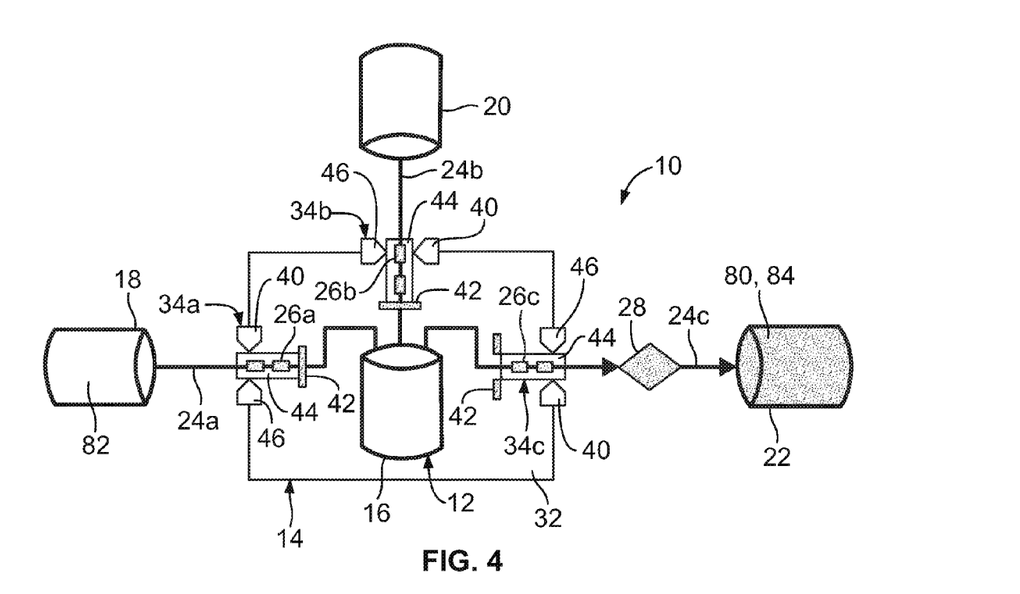
FIG. 4 illustrates the application of pressure to a container in the pressure chamber of FIG. 1 to express fluid out of the container and through a filtration device.
Figure 5:
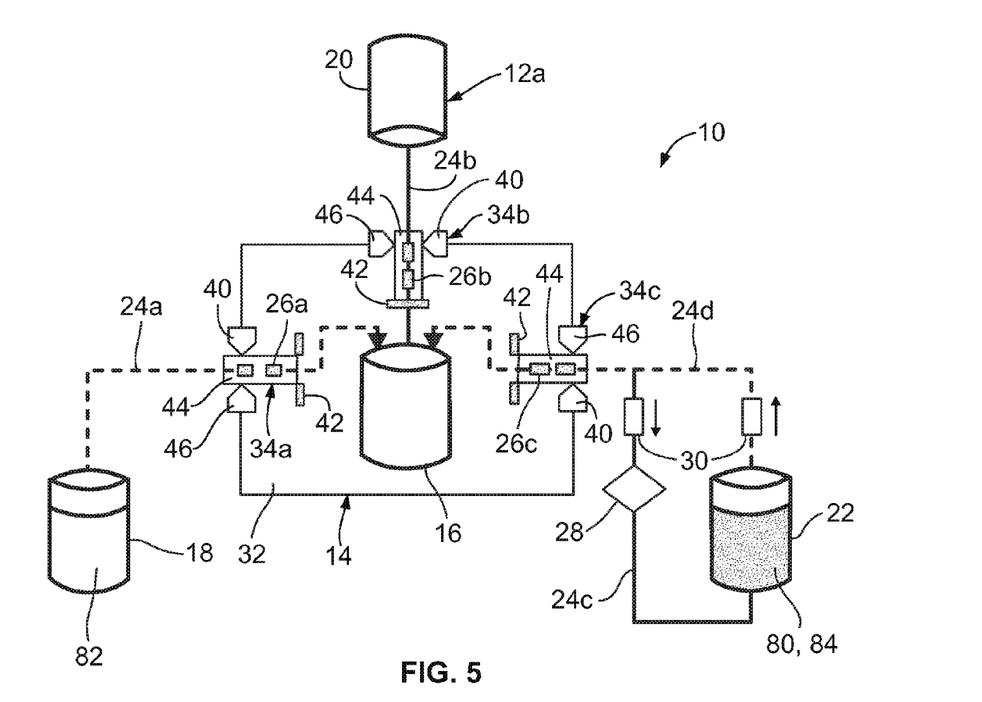
FIG. 5 illustrates the pressure chamber of FIG. 1 with an alternative flow circuit and the application of a vacuum to a container in the pressure chamber to remove air from another container.

The controller actuates the automated access device 46 associated with the conduit 24c from the red cell product container 22 to operate or break the associated closure device 26c (FIG. 4). Operating the closure device 26c allows for fluid communication between the whole blood collection container 16 and the red cell product container 22, although the clamping device 42 temporarily prevents any fluid flow.

The controller then commands the pressure/vacuum source 48 to increase the pressure in the interior 32 of the pressure chamber 14 to a desired level above atmospheric pressure. The pressure sensor 64 monitors the pressure in the pressure chamber 14 and sends a signal to the controller when the pressure reaches the desired level.

With the pressure inside the pressure chamber 14 at the desired level, the controller commands the clamping device 42 to disengage from the associated conduit 24c, thereby opening fluid communication between the whole blood collection container 16 and the red cell product container 22. On account of the pressure difference between the two containers 16 and 22, fluid is pushed out of the whole blood collection container 16 and into the red cell product container 22 via the conduit 24c (FIG. 4). The fluid (the RBC layer 84 mixed with additive solution 80) passes through the filtration device 28, where selected substances are removed therefrom. In one embodiment, the filtration device 28 comprises a leukofilter, which substantially removes white blood cells from the RBC layer 80. Different types of filtration or treatment devices may also be employed without departing from the scope of the present disclosure. A benefit of expressing the RBC layer 84 through the filtration device 28 under pressure is that it expedites filtration and also eliminates the need for a particular head height, so a shorter length of tubing may be used, which reduces the size and expense of the flow circuit 12 compared to disposable sets which use gravity-based filtration.

The operational state of FIG. 4 is maintained until the interface detector 40 associated with the conduit 24c senses a change in the nature of the light passing through the conduit 24a, such as by observing a significant increase in the amount of light transmitted through the conduit 24c. This significant increase in light transmission is indicative of a transition from the RBC layer 84 to air (or to the absence of red blood cells) flowing through the conduit 24c. When the interface detector 40 detects the transition, it sends a signal to the controller, which actuates the clamping device 42 to close fluid flow through the conduit 24c. If provided, the controller may actuate the automated sealing device 44 associated with the port 34c to irreversibly seal the conduit 24c between the containers 16 and 22. At this point, the red cell product container 22 and the plasma product container 18 are ready for long-term storage and the remainder of the flow circuit 12 can be unloaded from the pressure chamber 14 and discarded.

6. Automated Air Expression

While systems according to the present disclosure are well-suited for expressing liquid fluid, they may also be used for expressing gaseous fluids from or into a container. For example, as a result of the manufacturing process, an amount of air may generally be resident in the flow circuit 12 and, prior to long-term storage of the plasma and cellular blood components, it is often preferred to remove air from the plasma and/or red cell product containers 18 and 22. This may be achieved using either known manual methods (e.g., "burping" the containers 18 and 22 by squeezing them until the air has been removed) or by using novel methods made possible by systems according to the present disclosure.

To express air from the plasma product container 18, an additional step is incorporated into the above procedure prior to sealing the conduit 24a. After the clamping device 42 has been actuated to close the conduit 24a, but before the conduit 24a has been sealed, the controller commands the pressure/vacuum source 48 to decrease the pressure in the interior 32 of the pressure chamber 14 to a desired level below atmospheric pressure. The pressure sensor 64 monitors the pressure in the pressure chamber 14 and sends a signal to the controller when the pressure reaches the desired level.

With the pressure inside the pressure chamber 14 at the desired level, the controller commands the clamping device 42 to disengage from the associated conduit 24a, thereby reopening fluid communication between the whole blood collection container 16 and the plasma product container 18. On account of the pressure difference between the two containers 16 and 18, fluid is drawn or suctioned out of the plasma product container 18 and into the whole blood collection container 16 via the conduit 24a. By orienting the plasma product container 18 so as to place the conduit 24a at the top edge of the plasma product container 18 (i.e., oriented such that gravity acts in a direction generally extending from the edge including the conduit 24a to the opposite edge of the container 18), it will be the air above the plasma layer 82 that is first expressed or drawn out of the plasma product container 18.

Air continues flowing out of the plasma product container 18 until the interface detector 40 associated with the conduit 24a senses a change in the nature of the light passing through the conduit 24a, such as by observing a significant decrease in the amount of light transmitted through the conduit 24a. This significant decrease in light transmission is indicative of a transition from air to plasma flowing through the conduit 24a. When the interface detector 40 detects the transition, it sends a signal to the controller, which actuates the clamping device 42 to close fluid flow through the conduit 24a. At this time, the controller may actuate the automated sealing device 44 associated with the port 34a to irreversibly seal and optionally sever the conduit 24a between the containers 16 and 18, thereby leaving the plasma layer 82 in the plasma product container 18 with substantially no excess air therein.

A similar procedure may not be suitable for removing air from the red cell product container 22, as it requires back-pumping through the filtration device 28, which is undesirable for a number of reasons. For example, back-pumping can strand red cells between the filtration device 28 and the interface detector 40, thereby decreasing the red cell yield. Further, the undesirable substances (e.g., leukocytes) trapped in the filtration device 28 may become dislodged and migrate into the red cell product container 22.

Accordingly, to avoid the need for back-pumping through the filtration device 28, an alternative flow circuit 12a (FIG. 5) may be provided. Compared to the flow circuit 12 of FIGS. 1-4, the flow circuit 12a of FIG. 5 has an additional conduit 24d, with the conduit 24d being connected at its ends to conduit 24c (at a point between the filtration device 28 and the port 34c) and the top of the red cell product container 22. Each of the conduits 24c and 24d is provided with a one-way valve 30, with the valves 30 arranged so as to allow fluid flow in only the directions shown in FIG. 5. Hence, when expressing the RBC layer 84 into the red cell product container 22, the valves 30 force the fluid to pass through conduit 24c and the associated filtration device 28. Similarly, when expressing fluid out of the red cell product container 22 (as will be described in greater detail below) the valves 30 force the fluid to pass through conduit 24d, thereby bypassing the filtration device 28.

Up to the point of sealing the conduit 24c, the method of using the flow circuit 12a of FIG. 5 may be the same as described above with regard to the flow circuit 12 of FIGS. 1-4. Prior to sealing the conduit 24c, but after the clamping device 42 has been actuated to close the conduit 24c, the controller commands the pressure/vacuum source 48 to decrease the pressure in the interior 32 of the pressure chamber 14 to a desired level below atmospheric pressure. The pressure sensor 64 monitors the pressure in the pressure chamber 14 and sends a signal to the controller when the pressure reaches the desired level.

With the pressure inside the pressure chamber 14 at the desired level, the controller commands the clamping device 42 to disengage from the associated conduit 24c, thereby reopening fluid communication between the whole blood collection container 16 and the red cell product container 22. On account of the pressure difference between the two containers 16 and 22, fluid is drawn or suctioned out of the red cell product container 22 through conduit 24d (bypassing the filtration device 28) and into the whole blood collection container 16. With the conduit 24d entering through the top of the red cell product container 22, it will be the air above the RBC layer 84 that is expressed or drawn out of the red cell product container 22.

Air continues flowing out of the red cell product container 22 until the interface detector 40 associated with the conduit 24c senses a change in the nature of the light passing through the conduit 24a, such as by observing a significant decrease in the amount of light transmitted through the conduit 24c. This significant decrease in light transmission is indicative of a transition from air to red cells flowing through the conduit 24c. When the interface detector 40 detects the transition, it sends a signal to the controller, which actuates the clamping device 42 to close fluid flow through the conduit 24c. At this time, the controller may actuate the automated sealing device 44 associated with the port 34c to irreversibly seal the conduit 24c between the containers 16 and 22, thereby leaving the RBC layer 84 in the red cell product container 22 with substantially no excess air therein.

As shown in FIG. 5, air may be simultaneously removed from the plasma and red cell product containers 18 and 22 by (prior to sealing either conduit 24a, 24c) by applying a vacuum inside of the pressure chamber 14 and opening the respective conduits 24a and 24c. This may be preferred to individually expressing air from the containers 18 and 22 because it will decrease the overall processing time.

7. Mixing Red Cells

If desired, the step illustrated in FIG. 3 may be modified to more actively mix the additive solution 80 and RBC layer 84. After the additive solution 80 has been initially drawn into the whole blood collection container 16, the conduit 24b may remain open and the controller may cycle the pressure/vacuum source 48 between an elevated pressure and a vacuum. When the pressure is elevated, the additive solution 80 and RBC layer 84 will be expressed from the whole blood collection container 16 into the additive solution container 20. When the pressure inside the pressure chamber 14 is brought below atmospheric pressure, the additive solution 80 and RBC layer 84 will be expressed from the additive solution container 20 into the whole blood collection container 16. By cycling between the two states, the additive solution 80 and RBC layer 84 will be better mixed prior to expressing the mixture into the red cell product container 22. The sequence may be repeated a certain number of times or for a predetermined amount of time or based on some other predetermined endpoint (e.g., when the interface detector 40 associated with conduit 24b registers a particular reading).

D. Three-Component Processing

Figure 9:
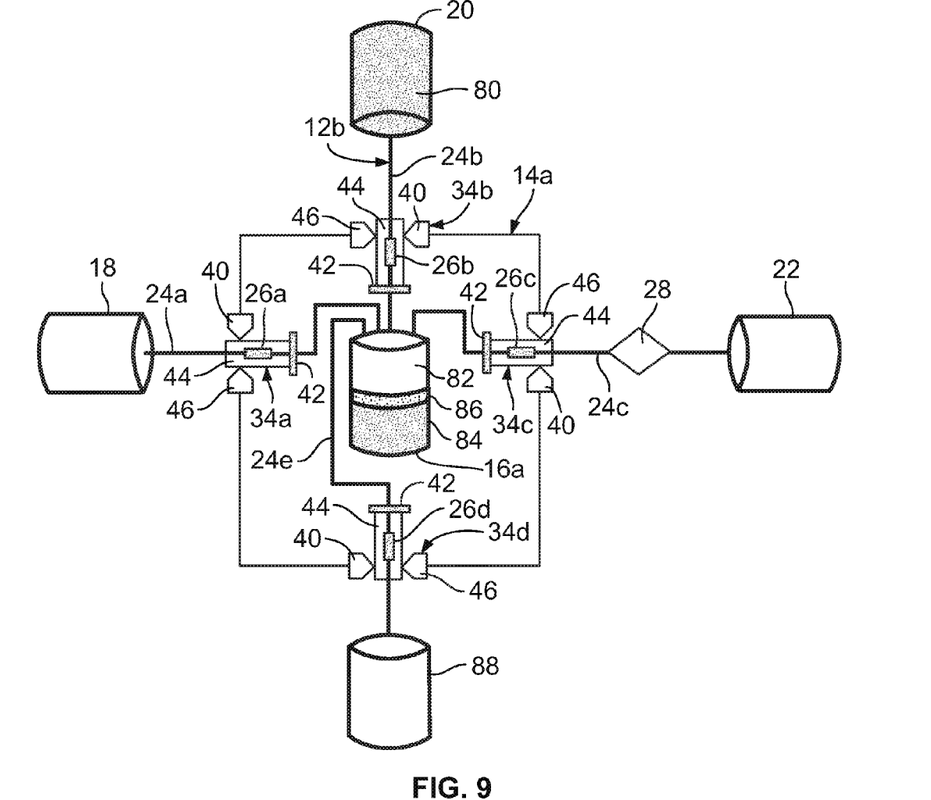
FIG. 9 is a diagrammatic view of an exemplary pressure chamber and flow circuit according to another aspect of the present disclosure.
Figure 10:
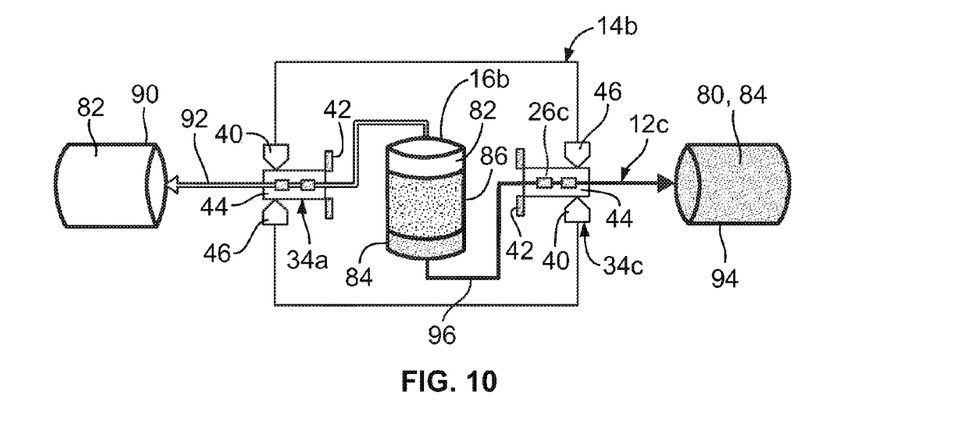
FIG. 10 is a diagrammatic view of an exemplary pressure chamber and flow circuit according to yet another aspect of the present disclosure.

FIGS. 9 and 10 illustrate flow circuits 12b and 12c, respectively, and pressure chambers 14a and 14b, respectively, suitable for processing of blood separated into three components: a plasma layer 82, an RBC layer 84, and a platelet or buffy coat layer 86.

The flow circuit 12b of FIG. 9 is identical to the flow circuit 12 of FIGS. 1-4, except it includes an additional conduit 24e which connects the whole blood collection container 16a to an additional container 88, which is referred to herein as the platelet product container. The pressure chamber 14a of FIG. 9 is identical to the pressure chamber 14 of FIGS. 1-4, except it includes a fourth port 34d, which accommodates the extra conduit 24e of the flow circuit 12b.

The blood in the whole blood collection container 16a is separated into a top plasma layer 82, a middle platelet layer 86, and a bottom RBC layer 84. The pressure in the pressure chamber 14a is increased to express the plasma layer 82 into the plasma product container 18 as described above with regard to FIG. 2.

When the interface detector 40 associated with conduit 24a detects a change in the nature of light passing through the conduit 24a, the associated clamping device 42 is actuated by the controller to close the conduit 24a. The change detected by the interface detector 40 is the transition from plasma to platelets in the conduit 24a. Thereafter, the closure element 26d associated with conduit 24e may be opened, followed by the associated clamping device 42 being opened, which allows the platelet layer 86 to flow through the conduit 24e and into the platelet product container 88.

When the interface detector 40 associated with conduit 24e detects a change in the nature of light passing through the conduit 24e, the associated clamping device is actuated by the controller to close the conduit 24e. The change detected by the interface detector 40 is the transition from platelets to red cells in the conduit 24e. Thereafter, additive solution 80 may be added to the RBC layer 84 in the whole blood collection container 16a as described above with regard to FIG. 3 and the RBC layer 84 may be filtered as described above with regard to FIG. 4.

As for the flow circuit 12c of FIG. 10, it is similar to the flow circuit 12 of FIGS. 1-4, except it employs a "top-bottom" whole blood collection container 16b which is connected to an upper container 90 by an upper conduit 92 connected to the upper end of the collection container 16b and a lower container 94 by a lower conduit 96 connected to the lower end of the collection container 16b. The pressure chamber 14b of FIG. 9 is identical to the pressure circuit 14 of FIGS. 1-4, except it omits one of the ports 34b.

The blood in the whole blood collection container 16b is separated into a top plasma layer 82, a middle platelet or buffy coat layer 86, and a bottom RBC layer 84. The pressure in the pressure chamber 14b is increased to sequentially or (as shown in FIG. 10) simultaneously express the plasma layer 82 into the upper container 90 (generally as described above with regard to FIG. 2) and the RBC layer 84 into the lower container 94 (generally as described above with regard to FIG. 4). The lower container 94 may include an amount of additive or red cell preservative solution 80, which is mixed with the RBC layer 84 as it is expressed out of the whole blood collection container 16b. When the interface detector 40 associated with the upper conduit 92 detects a change in the nature of light passing through the conduit 92 (signaling the transition from plasma to platelets), the associated clamping device 42 is actuated by the controller to close the conduit 92. Independently, the interface detector 40 associated with the lower conduit 96 monitors the nature of light passing therethrough and, when it detects a change (signaling the transition from red cells to platelets or buffy coat), the associated clamping device 42 is actuated by the controller to close the conduit 96. Thereafter, the upper and lower conduits 92 and 96 may be sealed, resulting in plasma being stored in the upper container 90, platelets being stored in the whole blood collection container 16b, and red cells stored in the lower container 94.

E. Additional Aspects and Implementations

Aspects of the present subject matter described above may be beneficial alone or in combination with one or more other aspects. Without limiting the foregoing description, in accordance with one aspect of the subject matter herein, there is provided a system for controlling fluid flow in a flow circuit of the type including at least two flexible containers and at least one conduit, wherein each container is fluidly connected to at least one other container by a conduit. The system includes a pressure chamber having an interior adapted to receive at least one of the containers of the flow circuit and at least one port communicating between the interior of the pressure chamber and the outside environment and adapted to receive at least a portion of one of the conduits of the flow circuit. The pressure chamber further includes a pressure/vacuum source associated with the pressure chamber for providing a pressure in the interior of the pressure chamber ranging between above atmospheric pressure and below atmospheric pressure and for changing the pressure in the interior of the pressure chamber.

In accordance with another aspect which may be used or combined with the preceding aspect, the system further includes an interface detector, an automated clamping device, an automated sealing device, and an automated access device associated with the port. A controller of the system is programmed to control the interface detector, the automated clamping device, the automated sealing device, the automated access device, and the pressure/vacuum source.

In accordance with another aspect which may be used or combined with any of the preceding aspects, the pressure chamber is configured to be moved to different locations.

In accordance with another aspect which may be used or combined with the first or second above aspects, the pressure chamber is configured to be installed and remain in a single location.

In accordance with another aspect which may be used or combined with any of the preceding aspects, the pressure chamber includes a plurality of ports. Each port includes an associated interface detector, automated clamping device, automated sealing device, and automated access device. The interface detector, automated clamping device, automated sealing device, and automated access device of each port is configured to be operated independently of the interface detectors, automated clamping devices, automated sealing devices, and automated access devices associated with the other ports.

In accordance with another aspect which may be used or combined with any of the preceding aspects, the system further includes a plurality of pressure chambers, with all of the pressure chambers being associated with a single pressure/vacuum source.

In accordance with another aspect which may be used or combined with the preceding aspect, the plurality of pressure chambers are configured to be operated independently of each other.

In accordance with another aspect, there is provided a method of controlling fluid flow in a flow circuit. The method includes providing a flow circuit including a plurality of flexible containers fluidly connected by a plurality of conduits, wherein at least one of the containers includes a fluid. At least one of the containers is inserted into a pressure chamber programmable to have an interior pressure in a range between greater than atmospheric pressure and less than atmospheric pressure. At least one of the other containers is positioned outside of the pressure chamber. A vacuum or positive pressure is applied to the at least one container in the pressure chamber, thereby expressing fluid from one of the fluid-containing containers to at least one of the other containers through one of the conduits.

In accordance with another aspect which may be used or combined with the preceding aspect, inserting one of the containers into a pressure chamber includes inserting one of the fluid-containing containers into the pressure chamber.

In accordance with another aspect which may be used or combined with the preceding aspect, applying a vacuum or positive pressure to the container in the pressure chamber includes applying a positive pressure to the fluid-containing container in the pressure chamber.

In accordance with another aspect which may be used or combined with any of the preceding three aspects, the method further includes monitoring the fluid in at least one of the conduits during expression of fluid therethrough and detecting the presence of a different fluid therein. The expression of fluid through the conduit is prevented when the presence of a different fluid in the conduit is detected.

In accordance with another aspect which may be used or combined with any of the preceding four aspects, at least one of containers positioned outside of the pressure chamber contains an additive solution and the method includes applying a vacuum to the at least one container in the pressure chamber, thereby expressing at least a portion of the additive solution into at least one of the containers in the pressure chamber.

In accordance with another aspect which may be used or combined with any of the preceding five aspects, the method includes detecting the presence of air in one of the conduits and applying a vacuum to the at least one container in the pressure chamber, thereby expressing air from the conduit into at least one of the containers in the pressure chamber.

In accordance with another aspect which may be used or combined with any of the preceding six aspects, the method includes filling one of the containers with an amount of blood and separating the blood into two or more blood components prior to inserting the blood component-containing container into the pressure chamber.

In accordance with another aspect, any of the methods of the preceding seven aspects may be carried out using any of the systems of the first seven above aspects.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A system for expressing fluids and controlling fluid flow in a flow circuit of the type including at least two flexible containers and at least one conduit, wherein each container is fluidly connected to at least one other container by a conduit, the system comprising:
    a pressure chamber having
        an interior adapted to receive at least one of the containers of the flow circuit,
        at least one port communicating between the interior of the pressure chamber and the outside environment and adapted to receive at least a portion of one of the conduits of the flow circuit,
        an interface detector associated with the port,
        an automated clamping device associated with the port,
        an automated sealing device associated with the port,
        an automated access device associated with the port, and
        a pressure/vacuum source associated with the pressure chamber for providing a pressure in the interior of the pressure chamber ranging between above atmospheric pressure and below atmospheric pressure and for changing the pressure in the interior of the pressure chamber; and a controller programmed to control the interface detector, the automated clamping device, the automated sealing device, the automated access device, and the pressure/vacuum source.

2. The system of claims 1, wherein the pressure chamber is configured to be moved to different locations.

3. The system of claim 1, wherein the pressure chamber is configured to be installed and remain in a single location.

4. The system of claim 1, wherein
the pressure chamber includes a plurality of ports,
each port includes an associated interface detector, automated clamping device, automated sealing device, and automated access device, and
the interface detector, automated clamping device, automated sealing device, and automated access device of each port is configured to be operated independently of the interface detectors, automated clamping devices, automated sealing devices, and automated access devices associated with the other ports.

5. The system of claim 1, further comprising a plurality of pressure chambers, wherein all of the pressure chambers are associated with a single pressure/vacuum source.

6. The system of claim 5, wherein the plurality of pressure chambers are configured to be operated independently of each other.

7. The system of claim 4, wherein
an access into the interior of the pressure chamber is defined by a generally quadrilateral perimeter having four sides,
the pressure chamber includes three ports, and each port is associated with a different one of said four sides.

8. The system of claim 1, wherein the interface detector, the automated clamping device, the automated sealing device, and the automated access device are integrated into a single subassembly.

9. The system of claim 1, wherein at least one of the interface detector, the automated clamping device, the automated sealing device, and the automated access device is incorporated into a first subassembly and at least another one of the interface detector, the automated clamping device, the automated sealing device, and the automated access device is incorporated into a second subassembly.

10. The system of claim 1, wherein the automated access device is configured to break a frangible cannula associated with said one of the conduits of the flow circuit.

11. The system of claim 1, further comprising a plurality of pressure chambers and a mounting stand, wherein each of the pressure chambers is mounted on the mounting stand.

12. The system of claim 1, further comprising a plurality of pressure chambers, wherein each pressure chamber is associated with the controller.

13. The system of claim 1, further comprising a plurality of pressure chambers, wherein each pressure chamber includes an associated controller.

14. The system of claim 1, further comprising a control panel incorporated into the pressure chamber.

15. The system of claim 1, wherein the pressure chamber includes one or more exterior hangers configured to support a flexible container of the flow circuit positioned outside of the interior of the pressure chamber.

* * * * *